United States Patent [19]

Kurkov

[11] 4,344,896

[45] Aug. 17, 1982

[54] PREPARATION OF 2-CYANOALDEHYDES BY RHODIUM-CATALYZED HYDROFORMYLATION

[75] Inventor: Victor P. Kurkov, San Rafael, Calif.

[73] Assignee: Chevron Research Company, San Francisco, Calif.

[21] Appl. No.: 128,016

[22] Filed: Mar. 7, 1980

Related U.S. Application Data

[63] Continuation-in-part of Ser. No. 11,272, Feb. 12, 1979, abandoned.

[51] Int. Cl.³ .................. C07C 120/00; C07C 121/34; C07C 121/46
[52] U.S. Cl. .................. 260/465.1; 260/464; 260/465.7
[58] Field of Search .................. 260/465.1, 464, 465.7

[56] References Cited

U.S. PATENT DOCUMENTS

| | | | |
|---|---|---|---|
| 3,527,809 | 9/1970 | Pruett et al. | 260/465.1 X |
| 3,579,562 | 5/1971 | Weigert et al. | 260/465.1 |
| 3,946,082 | 3/1976 | McVicker | 260/465.1 X |
| 4,052,461 | 10/1977 | Tinker et al. | 260/465.1 X |

*Primary Examiner*—Joseph Paul Brust
*Attorney, Agent, or Firm*—D. A. Newell; T. G. DeJonghe; C. J. Caroli

[57] ABSTRACT

Alpha,beta-unsaturated nitriles are hydroformylated to produce 2-cyanoaldehydes by means of a catalyst comprising rhodium complexed with carbon monoxide and a triorgano ligand of phosphorus, antimony or arsenic.

8 Claims, No Drawings

PREPARATION OF 2-CYANOALDEHYDES BY RHODIUM-CATALYZED HYDROFORMYLATION

CROSS-REFERENCE TO RELATED APPLICATION

This is a continuation-in-part of application Ser. No. 11,272, filed Feb. 12, 1979, now abandoned.

BACKGROUND OF THE INVENTION

The process of this invention concerns the hydroformylation of alpha,beta-unsaturated nitriles to produce the corresponding 2-cyanoaldehydes. In particular, the process of the invention concerns the use of a rhodium-ligand catalyst complex to produce selectively the 2-cyanoaldehydes from the alpha,beta-unsaturated nitriles.

The alpha,beta-unsaturated nitriles, such as acrylonitrile, have been hydroformylated previously. British Pat. No. 910,767, granted Nov. 21, 1962, describes the hydroformylation of acrylonitrile using dicobalt octacarbonyl. The process produces a relatively high yield of 3-cyanopropionaldehyde. In addition to 3-cyanopropionaldehyde, various by-products are formed. Kato et al. (Ajinomoto Co., Kawasaki) report in "Kogyo Kagaku Zasshi" 65, 184–7 (1962) that the hydroformylation of acrylonitrile in methanol produces 3-cyanopropionaldehyde as the principal product, and propionitrile, propanol, gamma-hydroxybutyronitrile, propylamine, ammonia and possibly allylamine as by-products.

The 2-cyanoaldehydes are valuable solvents and chemical intermediates. For instance, 2-cyanopropionaldehyde can be hydrogenated and dehydrated to produce methacrylonitrile. There are several processes for preparing 2-cyanoaldehyde reported in the art. For instance, Pino et al. (Polytecnico, Milan), in "Rend. 1st Lombardo Sci., Pt. I, Classe Sci. Mat. e Nat." 88, 378–88 (1955) report the production of 2-cyanopropionaldehyde by the ring-opening reaction of beta-methylisoxazole. Borsche et al in "Annalen" 512, 97–111 (1934) report that the condensation of ethyl nitrile and ethyl formate produce 2-cyanopropionaldehyde.

In accordance with U.S. Pat. No. 3,579,562, alpha- and beta-formyl nitriles are also allegedly produced by the formylation of methacrylonitrile using uncomplexed metallic rhodium, ruthenium or iridium or their salts or oxides. It is stated in the aforesaid patent that when products are desired containing primarily the alpha-formyl compounds, the hydroformylation reaction should be conducted at temperatures below 100° C. On the other hand, when the beta-compounds are desired, it is stated that the hydroformylation reaction should be carried out at temperatures above 100° C.

SUMMARY OF THE INVENTION

It has now been found that 2-cyanoaldehydes can be produced in greatly preponderant proportions as compared with the isomeric 3-cyanoaldehydes by the hydroformylation reaction of alpha,beta-unsaturated nitriles in the presence of a catalyst comprising rhodium in complex combination with carbon monoxide and a triorgano compound of phosphorus, arsenic or antimony, provided that the temperature of the hydroformylation reaction is above 100° C., the carbon monoxide-hydrogen pressure being in the range 50 to 500 atmospheres.

DETAILED DESCRIPTION OF THE INVENTION

The process of this invention is based upon the discovery that rhodium complexed with a stabilizing ligand and carbon monoxide can be used at the specified conditions of temperature and pressure, to catalyze the hydroformylation of alpha,beta-unsaturated nitriles to produce 2-cyanoaldehydes in a ratio to 3-cyanoaldehydes of the order of 40 to 1 and higher. This discovery is particularly surprising in view of the fact that the Group VIII metal hydroformylation catalysts are generally regarded equivalent, and the fact that the preferred hydroformylation catalyst, namely cobalt carbonyl, is known to produce the 3-cyano isomers from alpha,beta-unsaturated nitriles rather than the 2-cyano compounds.

More specifically, the rhodium-containing hydroformylation catalyst herein contemplated, and more fully to be described below, is formed by complexing a rhodium compound with carbon monoxide and a ligand. This catalyst complexing may be effected before the hydroformylation reaction or may be effected simultaneously with the hydroformylation reaction process.

In accordance with this invention, it is essential that the hydroformylation be carried out in the presence of the ligand-complexed rhodium-containing hydroformylation catalyst, for, as stated, of all the metals of Group VIII, including cobalt, the results obtained are unique to the rhodium catalyst.

The rhodium-containing complexes suitable for practicing the invention may be prepared using known methods, as described, for example, in U.S. Pat. No. 3,239,569, herein incorporated by reference, directed to the preparation of the related cobalt-containing complexes. One method is to charge the desired ligand, e.g., triphenylphosphite, to a reactor containing the nitrile feedstock and rhodium. The rhodium may be metallic rhodium, rhodium carbonyl, a rhodium oxide, a rhodium inorganic or organic salt or rhodium complexed with an organic solubilizing agent, such as acetylacetonate, and the like. More specifically, rhodium acetylacetonate and rhodium salts of organic acids such as acetic, propionic, etc., may be employed. Rhodium oxides, acetylacetonates and carboxylates are especially desirable, since they are easily converted to the effective rhodium catalyst under the conditions of reaction. After charging of the rhodium, ligand and nitrile, the reactor is pressured with carbon monoxide and hydrogen and heated, whereupon the effective catalyst agent is produced and the hydroformylation reaction occurs.

Another method of preparing the rhodium-containing complex is to react rhodium carbonyl and ligand to produce the desired catalyst for subsequent use in the hydroformylation reaction.

The ligands of the present invention are compounds of phosphorus, arsenic and antimony. These compounds may be represented by the formula $M[-(O)_n-R]_3$ where M is phosphorus, arsenic or antimony, O is oxygen, n is 0 or 1 and R is a hydrocarbyl group which may be an alkyl group of 1 to 20 carbon atoms, an aryl group of 6 to 14 carbon atoms, an alkaryl group of 7 to 20 carbon atoms, or an aralkyl group of 7 to 20 carbon atoms. The hydrocarbyl groups represented by R may be substituted by unreactive substituents such as chlorine.

Typical radicals when R is alkyl are methyl, hexyl, dodecyl, eicosyl and 8-chlorooctyl; when R is aryl, phenyl, naphthyl, and 2,4-dichlorophenyl; when R is alkaryl, 4-isopropylphenyl, 2-methylphenyl and 2-chloro-4-methylnaphthyl; and when R is aralkyl, benzyl, 4-naphthylpropyl and 2-chlorobenzyl.

Examples of ligands are triphenylphosphite, tri-4-tolylphosphite, tri-4-chlorophenylphosphite, triethylphosphite, tri-n-butylphosphite, triphenylphosphine, tri-4-tolylphosphine, triphenylarsine, triethylarsine, triphenylstibene and tri-n-butylstibene. The preferred ligands are triphenylphosphite and tri-4-tolylphosphite.

The rhodium-containing complexes of the present invention have a ligand to rhodium mol ratio of 1:1 to 60:1, preferably 4:1 to 10:1.

Alpha,beta-unsaturated nitriles which are suitable feeds to produce 2-cyanoaldehydes by the process of this invention include, for example, the nitriles or mixtures of the nitriles described by the structural formula:

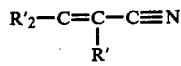

wherein each R' is independently selected from the group consisting of hydrogen; saturated organic radicals, such as alkyl of 1 to 6 carbon atoms and cycloalkyl of 5 to 6 carbon atoms; radicals, such as halide or nitro, provided that only one R' group is nitro. Representative specific nitriles suitable for use as feeds in the process of this invention include acrylonitrile, methacrylonitrile, 2-chloroacrylonitrile, crotononitrile, isocrotononitrile, angelonitrile, 3-methylcrotononitrile, 2-pentenenitrile, 2-ethylacrylonitrile or 2-methylenebutyronitrile, 2-ethylidenehexanonitrile, 2-butylcrotononitrile, 2-nitroacrylonitrile, 3-nitroacrylonitrile, and the like.

The hydroformylation reaction is carried out by contacting a suitable alpha,beta-unsaturated nitrile feed with carbon monoxide and hydrogen in the presence of a rhodium-containing catalyst complex under conventional hydroformylation conditions. The over-all reaction is depicted as follows:

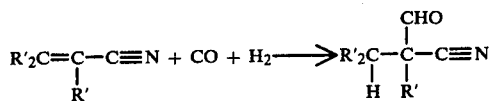

Hydroformylation conditions are familiar to those concerned with the hydroformylation reaction. The important reaction variables are temperature, carbon monoxide pressure, hydrogen pressure, and catalyst concentration. Suitable temperatures vary from above 100° C. to about 250° C., preferably from 120° C. to 200° C. Combined or total pressure of carbon monoxide and hydrogen generally varies from about 50 atmospheres to as much as about 500 atmospheres, preferably from about 75 atmospheres to about 150 atmospheres. In general, the carbon monoxide and hydrogen present in the reaction zone may range in a mol ratio of carbon monoxide to hydrogen of 4:1 to 1:4, preferably about 1:1. A convenient source of hydrogen and carbon monoxide is synthesis gas. For maximum conversion of nitrile to the desired product, there must be present in the reaction zone at least one mol of each gas for each mol of nitrile. In carrying out the reaction, it is generally preferred to operate with an excess of carbon monoxide and hydrogen in relation to the nitriles. Catalyst concentration generally varies from about 5 mol percent to as little as about 0.001 mol percent, preferably from about 1.0 mol percent to about 0.01 mol percent.

The hydroformylation reaction may be carried out neat or in the presence of an inert organic solvent. Examples of suitable solvents are hydrocarbons, such as pentanes, hexanes, benzene, toluene; alcohols, such as methanol, ethanol, propanol; ethers, such as diethylether, tetrahydrofuran; and nitriles, such as acetonitrile, benzonitrile. Alcohols, such as methanol and ethanol and propanol are preferred solvents because of high reaction rates and minimal side reactions such as hydrogenation of the double bond.

There are numerous processing techniques which are suitable for the process of this invention. However, certain processing steps are required to produce an economic product. These steps are: (1) the hydroformylation reaction itself; (2) removal of catalyst from the reaction mixture; (3) catalyst recovery and processing for reuse; and (4) product purification. There is great variation in the conditions and techniques used for each of the processing steps.

The reaction conditions selected and the reactor design for the hydroformylation step will vary to some extent with the type and amount of unsaturated feed. Two general types of reactors are used for hydroformylation reactions: back-mixed reactors where the composition of the reaction mixture approximates that of the product, and non-back-mixed or plug-flow reactors, where the composition of the reaction mixture changes with reaction time. More than one reactor in series may also be used.

The rhodium catalyst is preferably recovered in the active rhodium carbonyl form. This is readily accomplished when in accordance with the preferred embodiment the rhodium carbonyl is complexed with a ligand. Vacuum distillation of the product mixture results in the rhodium carbonyl-ligand complex appearing in the bottoms fraction. Alternatively, the rhodium may be recovered from the product by treatment with water at elevated temperatures, whereupon the rhodium components precipitate out in the aqueous phase, generally as a mixture of metallic rhodium and oxides thereof.

The aldehyde product may be purified by conventional distillation techniques. For the lower cyanoaldehydes, atmospheric pressure distillations can be used, and the products can be isolated in high purity. Steam distillations or extractive distillations with water are sometimes employed.

EXAMPLES

The following examples further illustrate the process of this invention and suggest alternative embodiments. Accordingly, the examples are not intended to limit the scope of the claims which follow. Unless stated otherwise, all parts are by weight.

EXAMPLE 1

A 300-ml stainless-steel autoclave was charged with 5.3 grams (0.1 mol) of acrylonitrile, 100 ml of methanol solvent, and a catalyst composed of 0.6 mmols of rhodium carbonyl acetylacetonate and 3.8 mmols of triphenylphosphite. Also charged to the autoclave was 8 grams of 1,2,4-trimethylbenzene as an internal gas chromatographic standard used to compute the § molar ratio. The autoclave was closed and then pressured to 80 atmospheres with synthesis gas containing equal amounts of hydrogen and carbon monoxide. The autoclave was brought up to 165 atmospheres by adding more of the same synthesis gas. Heating was continued for 1 hour.

Analysis by gas chromatography of the reactor contents at the end of this time showed an 84% conversion of acrylonitrile. Of the converted acrylonitrile, 84.9% was recovered as a 40:1 mixture of 2-cyanopropionaldehyde and 3-cyanopropionaldehyde respectively.

EXAMPLES 2-5

Other examples were carried out in essentially the same way with the temperature, carbon monoxide-hydrogen pressure and reaction times as shown in Table I. The catalyst composition in Example 2 was the same as in Example 1. The amount of triphenylphosphite was increased 10-fold in Example 3. In Example 4, the triphenylphosphite was replaced by an equal molar amount of triphenylphosphine. In Example 5, no ligand was used. The results of these examples are given in Table I.

TABLE I

| Ex. No. | Temp. °C. | Pressure atm. | Time hrs. | Conv. % | Selectivity[1] mol % | Ratio[2] |
|---|---|---|---|---|---|---|
| 1 | 130 | 165 | 1 | 84.1 | 84.9 | 40 |
| 2 | 130 | 35 | 1 | 62.2 | 21.9 | 0.4 |
| 3 | 130 | 35 | 1 | 69.0 | 43.6 | 2.1 |
| 4 | 130 | 185 | 0.5 | 100 | 32.4 | >40 |
| 5 | 103 | 190 | 1.5 | 100 | 21.3 | 2.4 |

[1]Selectivity to total aldehyde.
[2]Molar ratio of 2-cyanopropionaldehyde to 3-cyanoaldehyde

DISCUSSION OF THE EXAMPLES

Examples 1 and 2 demonstrate the effect of pressure on selectivity for the aldehydes and isomer distribution. As seen in Example 1, at 165 atmospheres pressure, with rhodiumtriphenylphosphite catalyst, 2-cyanopropionaldehyde is obtained in high selectivity. Lowering the pressure to 35 atmospheres, with the same catalyst system, gave much lower selectivity and also lower ⅔ ratio.

A somewhat higher selectivity was obtained in Example 3, which contained 10 times greater an amount of triphenylphosphite.

Example 4 shows the effect of triphenylphosphine as the catalyst modifier. As seen, it was not as good as triphenylphosphite, but it gave predominantly the branched isomer 2-cyanopropionaldehyde.

Example 5 shows the effect of ligand. In the absence of added ligands, both selectivity and the isomer ratio are low compared to Example 1.

What is claimed is:

1. A process for preparing 2-cyanoaldehydes by the hydroformylation reaction which comprises contacting an alpha,beta-unsaturated nitrile or mixture of such nitriles with carbon monoxide and hydrogen at a temperature from 130° C. to 250° C. and a combined carbon monoxide-hydrogen pressure of from 50 atmospheres to 500 atmospheres in the presence of a catalytic amount of a catalyst consisting essentially of rhodium in complex combination with carbon monoxide and a ligand; said alpha,beta-unsaturated nitrile being selected from the group consisting of compounds of the structural formula

wherein each R' is independently selected from the group consisting of hydrogen, saturated alkyl of 1 to 6 carbon atoms or cycloalkyl radicals of 5 to 6 carbon atoms, halide or nitro radicals, said compound having not more than one nitro group; and said ligand being represented by the formula $M[-(O)_n-R]_3$ where M is phosphorus, arsenic or antimony, O is oxygen, n is 0 or 1 and R is a hydrocarbyl radical selected from the group consisting of alkyl of 1 to 20 carbon atoms, aryl of 6 to 14 carbon atoms, alkaryl of 7 to 20 carbon atoms; or aralkyl atoms, and with the proviso that R may optionally be substituted by unreactive substituents; and wherein the molar ratio of 2-cyanoaldehydes to 3-cyanoaldehydes produced is at least of the order of 40 to 1.

2. The process according to claim 1 wherein the hydroformylation is carried out at a temperature of from about 130° C. to about 200° C. and a combined carbon monoxide-hydrogen pressure of from about 75 atmospheres to about 150 atmospheres.

3. The process according to claim 1 wherein the alpha,beta-unsaturated nitrile is acrylonitrile.

4. The process according to claim 1 wherein the alpha,beta-unsaturated nitrile is methacrylonitrile.

5. The process according to claim 1 wherein the ligand is triphenylphosphite.

6. The process according to claim 1 wherein the rhodium-containing hydroformylation catalyst is present at a concentration of from about 0.001 mol percent to about 5 mol percent.

7. The process according to claim 6 wherein the catalyst concentration is from about 0.01 mol percent to about 1 mol percent.

8. The process according to claim 1 wherein the carbon monoxide and hydrogen are present in the reaction zone in about equal molar quantities.

* * * * *

UNITED STATES PATENT AND TRADEMARK OFFICE
CERTIFICATE OF CORRECTION

PATENT NO. : 4,344,896
DATED : August 17, 1982
INVENTOR(S) : Victor P. Kurkov

It is certified that error appears in the above-identified patent and that said Letters Patent are hereby corrected as shown below:

Claim 1, col. 6, line 28, after "aralkyl", insert -- of 7 to 20 carbon --.

Signed and Sealed this

First Day of February 1983

[SEAL]

Attest:

Attesting Officer

GERALD J. MOSSINGHOFF
Commissioner of Patents and Trademarks